United States Patent [19]
Innis et al.

[11] Patent Number: 6,103,500
[45] Date of Patent: *Aug. 15, 2000

[54] PRODUCTION OF TISSUE FACTOR PATHWAY INHIBITOR

[75] Inventors: Michael A. Innis, Moraga; Abla A. Creasey, Piedmont, both of Calif.

[73] Assignee: Chiron Corporation, Emeryville, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/854,764

[22] Filed: May 12, 1997

Related U.S. Application Data

[63] Continuation of application No. 08/286,530, Aug. 5, 1994, abandoned.

[51] Int. Cl.[7] ............................ C12N 15/00; C07K 19/00
[52] U.S. Cl. .................. 435/69.7; 435/69.2; 435/254.11; 435/254.21; 530/412; 530/418; 930/250
[58] Field of Search .................. 435/69.2, 69.7, 435/254.11, 254.21; 530/412, 418; 930/250

[56] References Cited

U.S. PATENT DOCUMENTS

| | | | |
|---|---|---|---|
| 4,966,852 | 10/1990 | Wun et al. | 435/235.1 |
| 5,106,833 | 4/1992 | Broze, Jr. et al. | 514/12 |
| 5,212,091 | 5/1993 | Diaz-Collier et al. | 435/69.6 |
| 5,312,736 | 5/1994 | Rasmussen et al. | 435/69.2 |

FOREIGN PATENT DOCUMENTS

| | | |
|---|---|---|
| 473564 | 8/1991 | European Pat. Off. . |
| 93/14120 | 7/1993 | WIPO . |
| 93/14121 | 7/1993 | WIPO . |
| 93/14122 | 7/1993 | WIPO . |

OTHER PUBLICATIONS

Barr et al., *Recombinant Systems in Protein Expression* (1990) pp. 37–46.
Barr et al., *Expression Systems & Processes for rDNA Products* (1991) Chpt. 5:51–64.
Creasey et al., *J. Clin. Invest.* (1993) 91:2850–2860.
Finley, *The Molecular and Cellular Biology of the Yeast Saccharomyces: Gene Expression* (1992 2:539–581.
Hammamoto et al., *J. of Biol. Chem.* (1993) 268:8704–10.
Higuchi, PCR Protocols: *A Guide to Methods and Applications* (1990) Chpt. 22:177–183 (Innis et al. Eds.).
Lindhout et al., *J. Biochem.* (1994) 297:131–136.
Nakanishi–Shindo et al., *J. of Biol. Chem.* (1993) 268:26338–26345.
Petersen et al., *J. of Biol. Chem.* (1993) 268:13344–13351.
Sprecher et al., *PNAS (USA)* (1994) 91:3353–3357.
Cousens, L.S. et al. *Gene* 61:265–275 (1987).

*Primary Examiner*—Elizabeth Kemmerer
*Assistant Examiner*—David S. Romeo
*Attorney, Agent, or Firm*—Banner and Witcoff; Paul B. Savereide; Robert P. Blackburn

[57] ABSTRACT

A method for the production of Tissue Factor Pathway Inhibitor (TFPI) and Tissue Factor Pathway Inhibitor 2 (TFPI-2), and muteins thereof is disclosed wherein the protein is retained within a yeast cell during growth of the yeast cell and recovered from an insoluble fraction prepared from yeast cells containing the protein.

6 Claims, 4 Drawing Sheets

```
             5                      10                     15
Met Gln Ile Phe Val Lys Thr Leu Thr Gly Lys Thr Ile Thr Leu Glu
ATG CAG ATC TTC GTC AAG ACT TTG ACC GGT AAA ACC ATA ACA TTG GAA
TAC GTC TAG AAG CAG TTC TGA AAC TGG CCA TTT TGG TAT TGT AAC CTT 20                     25                     30
Val Glu Ser Ser Asp Thr Ile Asp Asn Val Lys Ser Lys Ile Gln Asp
GTT GAA TCT TCC GAT ACC ATC GAC AAC GTT AAG TCG AAA ATT CAA GAC
CAA CTT AGA AGG CTA TGG TAG CTG TTG CAA TTC AGC TTT TAA GTT CTG 35                     40                     45
Lys Glu Gly Ile Pro Pro Asp Gln Gln Arg Leu Ile Phe Ala Gly Lys
AAG GAA GGT ATC CCT CCA GAT CAA CAA AGA TTG ATC TTT GCC GGT AAG
TTC CTT CCA TAG GGA GGT CTA GTT GTT TCT AAC TAG AAA CGG CCA TTC 50                     55                     60
Gln Leu Glu Asp Gly Arg Thr Leu Ser Asp Tyr Asn Ile Gln Lys Glu
CAG CTA GAA GAC GGT AGA ACG CTG TCT GAT TAC AAC ATT CAG AAG GAG
GTC GAT CTT CTG CCA TCT TGC GAC AGA CTA ATG TTG TAA GTC TTC CTC 65                     70                     75                 80
Ser Thr Leu His Leu Val Leu Arg Leu Arg Gly Gly Asp Ser Glu Glu
TCC ACC TTA CAT CTT GTG CTA AGG CTC CGC GGT GGT GAT TCT GAG GAA
AGG TGG AAT GTA GAA CAC GAT TCC GAG GCG CCA CCA CTA AGA CTC CTT 85                     90                     95
Asp Glu Glu His Thr Ile Ile Thr Asp Thr Glu Leu Pro Pro Leu Lys
GAT GAA GAA CAC ACA ATT ATC ACA GAT ACG GAG TTG CCA CCA CTG AAA
CTA CTT CTT GTG TGT TAA TAG TGT CTA TGC CTC AAC GGT GGT GAC TTT 100                    105                    110
Leu Met His Ser Phe Cys Ala Phe Lys Ala Asp Asp Gly Pro Cys Lys
CTT ATG CAT TCA TTT TGT GCA TTC AAG GCG GAT GAT GGC CCA TGT AAA
GAA TAC GTA AGT AAA ACA CGT AAG TTC CGC CTA CTA CCG GGT ACA TTT 115                    120                    125
Ala Ile Met Lys Arg Phe Phe Phe Asn Ile Phe Thr Arg Gln Cys Glu
GCA ATC ATG AAA AGA TTT TTC TTC AAT ATT TTC ACT CGA CAG TGC GAA
CGT TAG TAC TTT TCT AAA AAG AAG TTA TAA AAG TGA GCT GTC ACG CTT 130                    135                    140
Glu Phe Ile Tyr Gly Gly Cys Glu Gly Asn Gln Asn Arg Phe Glu Ser
GAA TTT ATA TAT GGG GGA TGT GAA GGA AAT CAG AAT CGA TTT GAA AGT
CTT AAA TAT ATA CCC CCT ACA CTT CCT TTA GTC TTA GCT AAA CTT TCA 145                    150                    155                160
Leu Glu Glu Cys Lys Lys Met Cys Thr Arg Asp Asn Ala Asn Arg Ile
CTG GAA GAG TGC AAA AAA ATG TGT ACA AGA GAT AAT GCA AAC AGG ATT
GAC CTT CTC ACG TTT TTT TAC ACA TGT TCT CTA TTA CGT TTG TCC TAA
```

FIG. 3

| LANE | SAMPLE |
|---|---|
| 1 | MW MARKERS |
| 2 | PURIFIED YEAST TFPI 3 μg |
| 3 | WHOLE DISRUPATE |
| 4 | SUPERNATANT |
| 5 | FIRST WASH |
| 6 | SECOND WASH |
| 7 | INSOLUBLE FRACTION |
| 8 | INSOLUBLE FRACTION 5x LOAD |
| 9 | PURIFIED YEAST TFPI 3 μg |
| 10 | MW MARKERS |

PRODUCTION OF TISSUE FACTOR PATHWAY INHIBITOR

This application is a continuation, of application Ser. No. 08/286,530, filed Aug. 5, 1994, abandoned.

BACKGROUND OF THE INVENTION

The present invention relates to a method for the production of factor VIIa/TF/Xa binding proteins, more specifically to the production of Tissue Factor Pathway Inhibitor (TFPI) and Tissue Factor Pathway Inhibitor 2 (TFPI-2), and muteins thereof in yeast cells and isolation of such polypetides from within the yeast cell.

Tissue Factor Pathway Inhibitor (TFPI) inhibits the coagulation cascade in at least two ways: preventing formation of factor VIIa/tissue factor complex and by binding to the active site of factor Xa. The primary sequence of TFPI, deduced from cDNA sequence, indicates that the protein contains three Kunitz-type enzyme inhibitor domains. The first of these domains is required for the inhibition of the factor VIIa/tissue factor complex. The second Kunitz-type domain is needed for the inhibition of factor Xa. The function of the third Kunitz-type domain is unknown. TFPI has no known enzymatic activity and is thought to inhibit its protease targets in a stoichiometric manner; namely, binding of one TFPI Kunitz-type domain to the active site of one protease molecule. The carboxy-terminal end of TFPI is believed to have a role in cell surface localization via heparin binding and by interaction with phospholipid. TFPI is also known as Lipoprotein Associated Coagulation Inhibitor (LACI), Tissue Factor Inhibitor (TFI), and Extrinsic Pathway Inhibitor (EPI).

Mature TFPI is 276 amino acids in length with a negatively charged amino terminal end and a positively charged carboxy-terminal end. TFPI contains 18 cysteine residues and forms 9 disulphide bridges when correctly folded. The primary sequence also contains three Asn-X-Ser/Thr N-linked glycosylation consensus sites, the asparagine residues located at positions 145, 195 and 256. The carbohydrate component of mature TFPI is approximately 30% of the mass of the protein. However, data from proteolytic mapping and mass spectral data imply that the carbohydrate moieties are heterogeneous. TFPI is also found to be phosphorylated at the serine residue in position 2 of the protein to varying degrees. The phosphorylation does not appear to affect TFPI function.

TFPI has been shown to prevent mortality in a lethal *Escherichia coil (E. coli)* septic shock baboon model. Creasey el al, *J. Clin. Invest.* 91:2850–2860 (1993). Administration of TFPI at 6 mg/kg body weight shortly after infusion of a lethal dose of *E. coli* resulted in survival in all five TFPI-treated animals with significant improvement in quality of life compared with a mean survival time for the five control animals of 39.9 hours. The administration of TFPI also resulted in significant attenuation of the coagulation response, of various measures of cell injury and significant reduction in pathology normally observed in *E. coli* sepsis taret organs, including kidneys, adrenal glands, and lungs.

Due to its clot-inhibiting properties, TFPI may also be used to prevent thrombosis during microvascular surgery. For example, U.S. Pat. No. 5,276,015 discloses the use of TFPI in a method for reducing thrombogenicity of microvascular anastomoses wherein TFPI is administered at the site of the microvascular anastomoses contemporaneously with microvascular reconstruction.

Recently, another protein with a high degree of structural identity to TFPI has been identified. Sprecher et al, *Proc. Nat. Acad. Sci.*, USA 91:3353–3357(1994). The predicted secondary structure of this protein, called TFPI-2, is virtually identical to TFPI with 3 Kunitz-type domains, 9 cysteine-cysteine linkages, an acidic amino terminus and a basic carboxy-terminal tail. The three Kunitz-type domains of TFPI-2 exhibit 43%, 35% and 53% primary sequence identity with TFPI Kunitz-type domains 1,2, and 3, respectively. Recombinant TFPI-2 strongly inhibits the amidolytic activity of factor VIIa/tissue factor. By contrast, TFPI-2 is a weak inhibitor of factor Xa amidolytic activity.

TFPI has been isolated from human plasma and from human tissue culture cells including HepG2, Chang liver and SK hepatoma cells. Recombinant TFPI has been expressed in mouse C127 cells, baby hamster kidney cells, Chinese hamster ovary cells and human SK hepatoma cells. Recombinant TFPI from the mouse C127 cells has been shown in animal models to inhibit tissue-factor induced coagulation. Frequently, however, TFPI produced in mammalian cells is degraded by proteolytic cleavage. The protein is most often cleaved at the arginine at positions 83 and 199.

A non-glycosylated form of recombinant TFPI has been produced and isolated from *Escherichia coli (E. coli)* cells as disclosed in U.S. Pat. No. 5,212,091. This form of TFPI has been shown to be active in the inhibition of bovine factor Xa and in the inhibition of human tissue factor-induced coagulation in plasma. In some assays, the *E. coli*-produced TFPI has been shown to be more active than TFPI derived from SK hepatoma cells. However, TFPI produced in *E. coli* cells is frequently modified in ways that increase heterogeneity of the protein. These modifications include proteolytic degradation, carbamylation, and N-terminal modifications. Different forms of TFPI may also be found resulting from inappropriate internal translation initiation by *E. coli* ribosomes.

Methods have also been disclosed for purification of TFPI from yeast cell culture medium, such as in Petersen et al, *J.Biol.Chem.* 18:13344–13351 (1993). In these cases, recombinant TFPI is secreted from the yeast cell. TFPI recovered in such protocols is also frequently heterogeneous due perhaps to proteolytic degradation and variable glycosylation. Therefore, a need exists in the art to produce mature TFPI that is authentic (i.e. having the correct N-terminal amino acid sequence), full-length and homogeneous.

SUMMARY OF THE INVENTION

The invention relates to a method for producing factor VIIa/TF/Xa binding proteins, including TFPI, TFPI-2, and muteins thereof, the method including the steps of incubating yeast cells transformed with a replicable cloning vehicle, the replicable cloning vehicle comprising a first nucleotide sequence encoding the factor VIIa/TF/Xa binding protein, under conditions favorable for production of the factor VIIa/TF/Xa binding protein, wherein the factor VIIa/TF/Xa binding protein is retained within the yeast cell, preparing an insoluble fraction of the transformed yeast cells containing the factor VIIa/TF/Xa binding protein, and isolating the factor VIIa/TF/Xa binding protein contained in the insoluble fraction. The DNA encoding the factor VIIa/TF/Xa binding protein may be immediately preceded in frame by a second nucleotide seqence, the first and said second nucleotide sequences together encoding a fusion peptide, the fusion peptide capable of being cleaved within the yeast cells to produce authentic factor VIIa/TF/Xa binding protein. The second nucleotide sequence may encode ubiquitin. The yeast cells may be from the genus Saccharomyces, particularly Saccharomyces cerevisiae and may have a genotype selected from the group consisting of: VH6, AB122, and JSC310.

The invention also relates to the factor VIIa/TF/Xa binding protein produced by the method of the invention. Where the factor VIIa/TF/Xa binding protein is a mutein of TFPI, the mutein of TFPI may have an arginine in the $P_1$-reactive site of Kunitz-type domain 1.

BRIEF DESCRIPTION OF THE DRAWINGS

FIG. 3 depicts sequence encoding a ubiquitin-TFPI fusion protein [SEQ ID NO: 1] used to produce TFPI containing the authentic primary sequence in the method of the invention.

DETAILED DESCRIPTION OF THE INVENTION

Figure 1A:
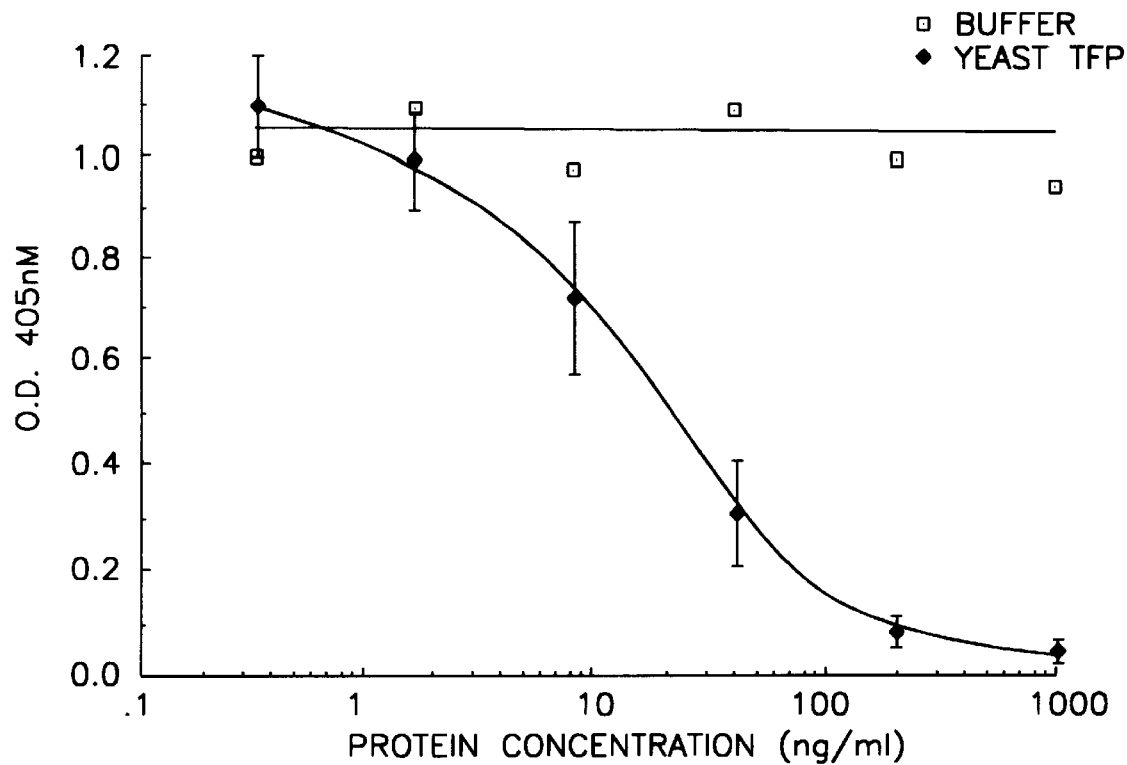
FIG. 1A and 1B show the activity of TFPI produced by the method of the invention.

As used herein, the term "factor VIIa/TF/Xa binding protein" refers to proteins capable of binding to the factor VIIa/TF complex thereby inhibiting the function of the complex and further capable of binding factor Xa thereby inhibiting its function. Full-length mature TFPI, TFPI-2 and muteins thereof are encompassed by this term. Preferably, the factor VIIa/TF/Xa binding protein is TFPI.

It has now been found that production of factor VIIa/TF/Xa binding proteins, specifically TFPI in yeast, wherein the TFPI is not secreted but is retained within the cells in an insoluble fraction, leads to recovery of authentic (i.e. having the correct N-terminal amino acid sequence), full-length and homogeneous TFPI. As used herein, the term "TFPI" refers to the 276 amino acid polypeptide as described in Girard et al, *Nature,* 338:518–520 (1989). As used herein, TFPI-2 refers to the 213 amino acid polypeptide as described in Sprecher et al, *Proc. Nat. Acad. Sci.*, USA 91:3353–3357 (1994).

Yeast expression systems that can be used in the present invention for the production of factor VIIa/TF/Xa binding protein are known to one of ordinary skill in the art. Such expression systems require, at a minimum, a yeast promoter which is a DNA sequence that is capable of binding yeast RNA polymerase and initiating the downstream (5'–3') transcription of a coding sequence (e.g. DNA encoding TFPI or TFPI-2) into mRNA. The promoter herein will have a transcription initiation region which is usually placed proximal to the 5' end of the coding sequence. This transcription initiation region usually includes an RNA polymerase binding site (the "TATA box") and a transcription initiation site. A yeast promoter herein may also have a second domain called an upstream activator sequence (UAS), which, if present, is usually distal to the structural gene (i.e. further upstream) relative to the transcription initiation region. The UAS also governs regulation of expression. Regulated expression may be either positive or negative, thereby either enhancing or reducing transcription as desired.

Yeast is a fermenting organism with an active metabolic pathway, therefore sequences encoding enzymes in the metabolic pathway provide particularly useful promoter sequences for the purpose of the present invention. Examples include alcohol dehydrogenase (ADH) (EPO Publ. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publ. No. 329 203). The yeast PHO5 gene, encoding acid phosphatase and described in Myanohara et al *Proc. Natl. Acad. Sci. USA* 80:1 (1983), also provides useful promoter sequences for the present invention.

In addition, synthetic promoters which do not occur in nature also function as yeast promoters herein. For example, UAS sequences of one yeast promoter may be joined with the transcription activation region of another yeast promoter, creating a hybrid promoter. Examples of such hybrid promoters include the ADH regulatory sequence linked to the GAP transcription activation region as described in U.S. Pat. Nos. 4,876,197 and 4,880,734, the disclosures of which are herein incorporated by reference. Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK, as described in EPO Publ. No. 164 556. Furthermore, a yeast promoter can include naturally occurring promoters of non-yeast origin that have the ability to bind yeast RNA polymerase and initiate transcription. Examples of such promoters include those described in the following references: Cohen et al, *Proc. Natl. Acad. Sci. USA* 77:1078 (1980); Henikoff et al, *Nature* 283:835 (1981); Hollenberg et al, *Curr. Topics Microbiol. Immunol.* (1981) 96:119; Hollenberg et al, "The Expression of Bacterial Antibiotic Resistance Genes in the Yeast *Saccharomyces cerevisiae,*" in: *Plasmids of Medical, Environmental and Commercial Importance* (eds. K. N. Timmis and A. Puhler) (1979); Mercerau-Puigalon et al, (1980) *Gene* 11:163; Panthier et al, *Curr. Genet.* 2:109 (1980).

The production of fusion proteins in a yeast expression system is preferred for the purpose of the present invention. More specifically, a DNA sequence encoding the N-terminal portion of an endogenous yeast protein, or other stable protein, is fused to the 5' end of the factor VIIa/TF/Xa binding protein encoding sequences. Upon expression, this construct will provide a fusion of the two amino acid sequences. For example, the yeast or human superoxide dismutase (SOD) gene, can be linked at the 5' terminus of the TFPI gene and the resulting fusion protein expressed in yeast. The DNA sequence at the junction of the two amino acid sequences may or may not encode a cleavable site as described in EPO Publ. No. 196 056. Preferably, the site is cleavable. A preferred fusion protein is a ubiquitin-TFPI fusion protein. Such a fusion protein is made with the ubiquitin sequence that preferably retains a site for a processing enzyme which allows a ubiquitin-specific processing protease to cleave the ubiquitin from the desired polypeptide. Through this method, therefore, mature factor VIIa/TF/Xa binding protein having an authentic amino terminus can be produced in and isolated from within the yeast cell. Use of the ubiquitin protein fusion technique is reviewed in Barr et al, in RECOMBINANT SYSTEMS IN PROTEIN EXPRESSION (Elsevier Science Publishers B.V., 1991), pp. 37–46.

Usually, transcription termination sequences recognized by yeast are regulatory regions located 3' to the translation stop codon and, together with the promoter, flank the coding sequence. These sequences direct the transcription of an mRNA which can be translated into the polypeptide encoded by the DNA. Yeast-recognized termination sequences from genes, such as those coding for alpha-factor and for glycolytic enzymes, can be used herein.

Usually, the above described components, comprising a promoter, optionally a leader, the factor VIIa/TF/Xa binding protein encoding sequence, and transcription termination sequence, are put together into expression constructs. Expression constructs herein can be maintained in a replicon, such as an extrachromosomal element (e.g., a plasmid) capable of stable maintenance in a host, such as yeast or bacteria. The replicon may have two replication systems, thus allowing the replicon to be maintained, for example, in yeast for expression and in a procaryotic host for cloning and amplification. Examples of such yeast-bacteria shuttle vectors that are useful herein include YEp24 as described in Botstein et al, (1979) *Gene* 8:17–24; pCl/l, as described in Brake et al, (1984) *Proc. Natl. Acad. Sci USA* 81:4642–4646; and YRp17, as described in Stinchcomb et al, (1982) *J. Mol. Biol.* 158:157. In addition, a replicon may be either a high or low copy number plasmid. A high copy number plasmid will generally have a copy number ranging from about 5 to about 200, and usually about 10 to about 150. Either a high or low copy number vector may be selected, depending upon the effect of the vector and the foreign protein on the host. See e.g., Brake et al, supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome. An integrating vector may be directed to a specific locus in yeast by selecting the appropriate homologous sequence for inclusion in the vector, as described in Orr-Weaver et al, *Methods in Enzymol.* 101:228–245 (1983). One or more expression construct may integrate, possibly affecting levels of recombinant protein produced. Rine et al, *Proc. Natl. Acad. Sci. USA* 80:6750 (1983). The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions as described in Butt et al, *Microbiol, Rev.* 51:351 (1987).

Alternatively, the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* (Kurtz, et al, Mol. Cell. Biol. 6:142 (1986)), *Candida maltosa* (Kunze, et al, J. Basic Microbiol. 25:141 (1985)), *Hansenula polymorpha* (Gleeson, et al, *J. Gen. Microbiol.* 132:3459 (1986); Roggenkamp et al, Mol. Gen. Genet. 202:302 (1986)), *Kluyveromyces fragilis* (Das, et al, *J. Bacteriol.* 158:1165 (1984)), *Kluyveromyces lactis* (De Louvencourt et al, J. Bacteriol. 154:737 (1983); Van den Berg et al, Bio/Technology 8:135 (1990)), *Pichia guillerimondii* (Kunze et al, J. Basic Microbiol. 25:141 (1985)), *Pichia pastoris* (Cregg, et al, Mol. Cell. Biol. 5:3376 (1985); U.S. Pat. Nos. 4,837,148 and 4,929,555), *Saccharomyces cerevisiae* (Hinnen et al, Proc. Natl. Acad. Sci. USA 75:1929 (1978); Ito et al, J. Bacteriol. 153:163 (1983)), *Schizosaccharomyces pombe* (Beach and Nurse, Nature 300:706 (1981)), and *Yarrowia lipolytica* (Davidow, et al, Curr. Genet. 10:380471 (1985) and Gaillardin, et al, Curr. Genet. 10:49 (1985)).

Transformation procedures that may be used herein to transform yeast cells include electroporation, as described in "Guide to Yeast Genetics and Molecular Biology," Vol 194 METHODS IN ENZYMOLOGY, C. Guthrie and G. R. Fink, (Academic Press 1991). Other procedures include the transformation of spheroplasts or the transformation of alkali cation-treated intact cells. Such procedures are described in, for example, Kurtz et al, *Mol. Cell. Biol.* 6:142 (1986); Kunze et al, *J. Basic Microbiol.* 25:141 (1985), for Candida; Gleeson et al, *J. Gen. Microbiol.* 132:3459 (1986); Roggenkamp et al., *Mol. Gen. Genet.* 202:302, for Hansenula (1986); Das et al, *J. Bacteriol.* 158:1165 (1984); De Louvencourt et al, *J. Bacteriol.* 154:1165 (1983); Van den Berg et al, *Bio/Technology* 8:135 (1990) for Kluyveromyces; Cregg et al, *Mol. Cell. Biol.* 5:3376 (1985); Kunze et al, *J. Basic Microbiol.* 25:141 (1985); U.S. Pat. No. 4,837, 148 and U.S. Pat. No. 4,929,555, for Pichia; Hinnen et al, *Proc. Natl. Acad. Sci. USA* 75:1929 (1978); Ito et al, *J. Bacteriol.* 153:163 (1983), for Saccharomyces; Beach and Nurse *Nature* 300:706 (1981), for Schizosaccharomyces; Davidow et al, *Curr. Genet.* 10:39 (1985); Gaillardin et al, *Curr. Genet.* 10:49 (1985), for Yarrowia.

Muteins of TFPI or TFPI-2 may also be prepared according to the method of the invention. Muteins within the scope of this definition include: (a) TFPI or TFPI-2 muteins having 1–5 conservative amino acid substitutions that do not substantially change the conformation of the molecule; (b) TFPI or TFPI-2 muteins with amino acid substitutions that eliminate one or more of the sites for N-linked glycosylation; (c) TFPI muteins having 1–5 amino acid substitutions that change a residue of TFPI to a corresponding residue of TFPI-2; (d) TFPI-2 inuteins having 1–5 amino acid substitutions that change a residue of TFPI-2 to a corresponding residue of TFP1; (e) TFPI or TFPI-2 muteins with amino acid substitutions in $P_1$-reactive sites in one or more Kunitz-type domains; and (f) TFPI or TFPI-2 muteins with amino acid substitutions at positions within 5 amino acids of the $P_1$-reactive sites in one or more Kunitz-type domains. In a preferred embodiment, the lysine residue in the $P_1$-reactive site of the first Kunitz-type domain of TFPI is replaced with arginine. The mutein has the following sequence:

```
Asp Ser Glu Glu Asp Glu Glu His Thr Ile Ile Thr Asp Thr Glu Leu  [SEQ ID NO: 3]

Pro Pro Leu Lys Leu Met His Ser Phe Cys Ala Phe Lys Ala Asp Asp

Gly Pro Cys Arg Ala Ile Met Lys Arg Phe Phe Asn Ile Phe Thr

Arg Gln Cys Glu Glu Phe Ile Tyr Gly Gly Cys Glu Gly Asn Gln Asn

Arg Phe Glu Ser Leu Glu Glu Cys Lys Lys Met Cys Thr Arg Asp Asn

Ala Asn Arg Ile Ile Lys Thr Thr Leu Gln Gln Glu Lys Pro Asp Phe

Cys Phe Leu Glu Glu Asp Pro Gly Ile Cys Arg Gly Tyr Ile Thr Arg

Tyr Phe Tyr Asn Asn Glu Thr Lys Gln Cys Glu Arg Phe Lys Tyr Gly

Gly Cys Leu Gly Asn Met Asn Asn Phe Glu Thr Leu Glu Glu Cys Cys

Asn Ile Cys Glu Asp Gly Pro Asn Gly Phe Gln Val Asp Asn Tyr Gly

Thr Gln Leu Asn Ala Val Asn Asn Ser Leu Thr Pro Gln Ser Thr Lys

Val Pro Ser Leu Phe Glu Phe His Gly Pro Ser Trp Cys Leu Thr Pro

Ala Asp Arg Gly Leu Cys Arg Ala Asn Glu Asn Arg Phe Tyr Tyr Asn

Ser Val Ile Gly Lys Cys Arg Pro Phe Lys Tyr Ser Gly Cys Gly Gly

Asn Glu Asn Asn Phe Thr Ser Lys Gln Glu Cys Leu Arg Ala Cys Lys

Lys Gly Phe Ile Gln Arg Ile Ser Lys Gly Gly Leu Ile Lys Thr Lys

Arg Lys Arg Lys Lys Gln Arg Val Lys Ile Ala Tyr Glu Glu Ile Phe

Val Lys Asn Met.
```

Similarly, the mutein may be a TFPI-2 mutein in which the glutamate residue in the $P_1$-reactive site of the second Kunitz-type domain of TFPI-2 is replaced with arginine. Production and isolation of muteins of TFPI and TFPI-2 in which one or more consensus sites for N-linked glycosylation have been altered to prevent such recognition is also within the method of the invention. TFPI has three such consensus sequences which may be altered for example by substituting alanine for serine or threonine in the the consensus site. Similarly, inuteins of TFPI-2 in which the serine residue at position 96 of mature TFPI-2 and/or the threonine residue at position 150 of mature TFPI-2 have been substituted with alanine may also be prepared. Muteins containing conservative amino acid substitutions relative to the sequence of TFPI or TFPI-2 may be produced and isolated according to the invention. Finally, production and isolation of muteins of TFPI in which the corresponding amino acid of TFPI-2 for a given site is substituted for the amino acid normally found in the TFPI sequence and muteins of TFPI-2 in which the corresponding amino acid of TFPI for a given site is substituted for the amino acid normally found in the TFPI sequence are within the scope of the invention.

Muteins may be prepared by appropriate mutagenesis of the sequence of the recombinant cloning vehicle encoding TFPI or TFPI-2. Techniques for mutagenesis include, without limitation, site specific mutagenesis. Site-specific mutagenesis can be carried out using any number of procedures known in the art. These techniques are described, for example, by Smith, 1985, *Annual Review of Genetics,* 19:423, and modifications of some of the techniques are described in *Methods in Enzymology,* 154, part E, (eds.) Wu and Grossman (1987), chapters 17, 18, 19, and 20. Site specific mutagenesis may also be carried out using the Gapped Duplex site-directed mutagenesis method. The general procedure is described by Kramer, et al., in chapter 17 of the *Methods in Enzymology,* supra. Other techniques for generating point mutations in a nucleic acid sequence PCR techniques, including overlapping PCR, are decribed in PCR PROTOCOLS: A GUIDE TO METHODS AND APPLICATIONS, (eds.) Innis, Gelfand, Sninsky and White (Academic Press, 1990).

Formulation and Administration

LACI made by the method of the invention may be administered at a concentration that is therapeutically effective to treat and prevent septic shock. To accomplish this goal, the LACI made by the method of the invention is preferably administered intravenously. Methods to accomplish this administration are known to those of ordinary skill in the art.

Before administration to patients, formulants may be added to the LACI made by the method of the invention. A liquid formulation may be used. For example, these formulants may include oils, polymers, vitamins, carbohydrates, amino acids, salts, buffers, albumin, surfactants, or bulking agents. Carbohydrates which may be used in the formulation include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof Sucrose is most preferred. Sugar alcohol is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to iminimize pH changes in the solution before lyophilization or after reconstitution. Most any physiological buffer may be used, but citrate, phosphate, succinate, and glutamate buffers or mixtures thereof are preferred. Most preferred is a citrate buffer. Further, the use of sulfates should be avoided in preparation of the formulation. Preferably, the concentration is from 0.01 to 0.3 molar. Surfactants that can be added to the formulation are shown in EP Nos. 270,799 and 268,110.

Additionally, the LACI made by the method of the invention can be chemically modified by covalent conjugation to a polymer to increase its circulating half-life, for example. Preferred polymers, and methods to attach them to peptides, are shown in U.S. Pat. Nos. 4,766,106, 4,179,337, 4,495,285, and 4,609,546 which are all hereby incorporated by reference in their entireties. Preferred polymers are polyoxyethylated polyols and polyethyleneglycol (PEG). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/LACI.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Bio. Chem.* 263:15064–15070, and a discussion of POG/protein conjugates is found in U.S. Pat. No. 4,766, 106, both of which are hereby incorporated by reference in their entireties.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

Administration to Affected Individuals

LACI made by the method of the invention is useful to treat mammals with sepsis or septic shock. Generally, conditions are characterized by high fever (>38.5° C.) or hypothermia (>35.5° C.), low blood pressure, tachypnea (>20 breaths/minute), tachycardia (>100 beats/minute), leukocytosis (>15,000 cells/mm$^3$) and thrombocytopenia (<100,000 platelets/mm3). The LACI made by the method of the invention is preferably administered as soon as the subject is suspected of being septic; presenting a >20% drop in fibrinogen or appearance of fibrin split products, a rise in the subject's temperature and the diagnosis of leukopenia and hypotension associated with septic shock. As stated above, intravenous administration is preferred. Generally, LACI made by the method of the invention is given at a dose between 1 µg/kg and 20 mg/kg, more preferably between 20 µg/kg and 10 mg/kg, most preferably between 1 and 7 mg/kg. Preferably, it is given as a bolus dose, to increase circulating levels by 10–20 fold and for 4–6 hours after the bolus dose. Continuous infusion may also be used after the bolus dose. If so, LACI may be infused at a dose between 5 and 20 µg/kg/minute, more preferably between 7 and 15 µg/kg/minute.

The LACI made by the method of the invention may be given in combination with other agents which would be effective to treat septic shock. For example, the following may be administered in combination with the LACI made by the method of the invention: antibiotics that can treat the underlying bacterial infection; monoclonal antibodies that are directed against bacterial cell wall components; monoclonal antibodies and soluble receptors that can complex with cytokines that are involved in the sepsis pathway, including, but not limited to tumor necrosis factor (TNF), Interleukin-1, γ-interferon and interleukin-8; and generally any agent or protein that can interact with cytokines or complement proteins in the sepsis pathway to reduce their effects and to attenuate sepsis or septic shock.

Antibiotics useful in the present invention include those in the general category of: beta-lactam rings (penicillin), amino sugars in glycosidic linkage (amino glycosides), macrocyclic lactone rings (macrolides), polycyclic derivatives of napthacenecarboxamide (tetracyclines), nitrobenzene derivatives of dichloroacetic acid, peptides (bacitracin, gramicidin, and polymyxin), large rings with a conjugated double bond system (polyenes), sulfa drugs derived from sulfanilarnide (sulfonamides), 5-nitro-2-furanyl groups (nitrofurans), quinolone carboxylic acids (nalidixic acid), and many others. Other antibiotics and more versions of the above specific antibiotics may be found in Encyclopedia of Chemical Technology, 3rd Edition, Kirk-Othymer (ed.), Vol. 2, pages 782–1036 (1978) and Vol. 3, pages 1–78, Zinsser, *MicroBiology,* 17th Edition W. Joklik et al (Eds.) pages 235–277 (1980), or Dorland's Illustrated Medical Dictionary, 27th Edition, W. B. Saunders Company (1988).

Other agents which may be combined with the LACI made by the method of the invention include monoclonal antibodies directed to cytokines involved in the sepsis pathway, such as those monoclonal antibodies directed to IL-6 or M-CSF, such as shown in PCT US90/07411; monoclonal antibodies directed to TNF, such as shown in U.S. Pat. No. 4,603,106; inhibitors of proteins that cleave the mature TNF prohormone from the cell in which it was produced, such as shown in PCT US90/03266 and PCT US93/06120; antagonists of IL-1, such as shown in PCT US91/02460; inhibitors of IL-6 cytokine action such as activin, such as shown in PCT US90/003 21; and receptor based inhibitors of various cytokine such as IL-1. Antibodies to or small molecule inhibitors of complement protein may also be employed.

Generally, the LACI made by the method of the invention may be useful for those diseases that occur due to the up-regulation of tissue factor brought on by injury, trauma, endotoxin, TNF, cancer, IL-1 or other agents or conditions.

The present invention will now be illustrated by reference to the following examples which set forth particularly advantageous embodiments. However, it should be noted that these embodiments are illustrative and are not to be construed as restricting the invention in any way.

EXAMPLES

Example 1

The shuttle vector pBS24 is described in Barr et al, EXPRESSION SYSTEMS & PROCESSES FOR rDNA PRODUCTS (American Chemical Society, 1991), pp 51–64). pBS24Ub is a derivative of pBS24.1, and contains an expression cassette flanked by unique Bam HI and Sal I restriction sites, the glucose regulatable ADH2/GAP promoter and a synthetic ubiquitin (Ub) gene. For construction of Ub fusions, a unique SstII site is generated in the 3' end of the Ub gene. The presence of the SstII site allows in-frame insertion of nucleotide sequences for expression as ubiquitin fusion peptides. Insertion can be accomplished by use of synthetic DNA adapters or PCR methodologies. In either case, the 5'-junction sequence will be:

```
  ARG GLY GLY                    [SEQ ID NO: 4]
C CGC GGY GGC
G GCG CCA CCG
    SstII
``` and the 3' cloning site (Sal I) should be as close as possible to the 3' end of the termination codon.

PCR was used to construct the ubiquitin/TFPI gene fusion in the 15.4 kb plasmid pLACI 4.1 shown in FIG. 3. TFPI encoding nucleic acid was amplified using standard PCR procedures with the primers LACI4 and LACI3. LACI4 hybridizes to the 10 nucleotides at the 5' end of nucleic acid mature encoding TFPI and also contains ubiquitin sequence with the SstII restriction site. LACI3 hybridizes to the 15 nucleotides at the 3' end of nucleic acid encoding mature TFPI and also trailing sequence with a Sal I restriction site. The sequences of these primers are as follows:

```
LACI4  GCTCCGCGGTGGCGATTCTGAGG    [SEQ ID NO:5]

LACI3  TCTGTCGACTCACATATTTTTAAC   [SEQ ID NO: 6]
```

After amplification, the PCR product was digested with Sal I and Sst II using conditions specified by the manufacturer of the enzymes. The digested PCR product was then cloned into pBS24Ub, as described above, to produce pLACI 4.1.

pLACI 4.1 was used to transform three strains of *Saccharomyces cerevisiae*: VH6 (MAT α, cir°, Leu-2-112, -3, ura3, FoA, pep4:His3), AB122 (Mat α, cir°, leu2, ura3-52, prb1-1112, pep4-3, prc1-407) and JSC310 (as AB122,+ ADR1 overexpression). Transformants of VH6 produced TFPI at levels of approximately 5% of total protein, transformants of AB122 produced TFPI at levels of approximately 10% of total protein and transformants of JSC310 produced TFPI at levels of approximately 15% of total protein. The stability of TFPI is somewhat surprising in view of prior studies showing that proteins synthesized as ubiquitin fusions and having N-terminal aspartate after removal of the ubiquitin are unstable in the yeast cell (e.g. half-life <3 min.). See Finley, "The Yeast Ubiquitin System" in: *The Molecular and Cellular Biology of the Yeast Saccharomyces: Gene Expression* (1992).

Example 2

Part A

Figure 4:
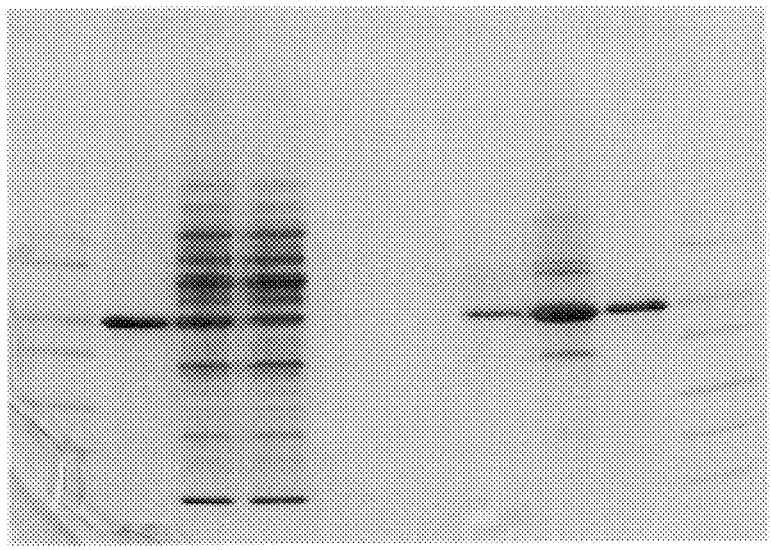
FIG. 4 shows a Coomassie stained PAGE gel of TFPI contained in an insoluble fraction within yeast cells after an initial purification.

TFPI was purified from *S. cerevisiae* VH6 cells according to the method disclosed in U.S. Pat. No. 5,212,091, which is herein incorporated by reference, specifically at columns 9–10. An insoluble fraction (also referred to as a membrane fraction) was prepared by Dyno-Mill glass bead extraction in TEN (50 nM Tris.HCl pH7.8; 50 mM NaCl, 5 mM EDTA). Approximately 3 μg of total protein from this fraction was run out on 14% SDS-PAGE gel and transferred to nitrocellulose membranes. The nitrocellulose blots were probed with rabbit polyclonal antisera generated to the first fifteen amino acids of the mature TFPI peptide sequence. The resulting blot (FIG. 5) shows a significant band of homogeneous, full-length TFPI. Expression of TFPI into the insoluble fraction was also verified using comparative Coomassie-stained 14% SDS-PAGE gels. (See FIG. 4). Yeast cells were grown with plasmid-containing DNA encoding the TFPI protein, or with the identical plasmid without DNA encoding the TFPI protein. Approximately 10 μg of yeast whole cell lysate or insoluble fraction from the two cultures was loaded onto the gel. A unique 36 kD band was detected only in the lanes prepared from cultures carrying the TFPI-producing plasmid.

Sulfonation and Q Sepharose® fractionation were performed as specified in U.S. Pat. No. 5,212,091. Refolding of the isolated TFPI was also performed essentially as described except that dialysis was performed in 5 M urea, 0.3 M NaCl, 20 mM Tris.HCl pH 7.8, 0.04% NP40, 2 mM L-cysteine, 0.5 mM EDTA for 4–6 at room temperature and then 4° C. overnight, after which dialysis bags were transferred to 2 M urea, 1 mM L-cysteine for 48 hours at 4° C. For S Sepharose® fractionation, the refolded TFPI was equilibrated in 2 M urea, 50 mM NaPO$_4$, 0.1 M NaCl prior to column loading. Wash buffer contained 2 M urea, 50 mM NaPO$_4$, 0.25 M NaCl and TFPI was step-eluted with buffer containing 2 M urea, 50 MM NaPO$_4$, 0.8 M NaCl. Fractions containing TFPI were pooled and dialyzed against PBS/1.5 M urea at 4° C. overnight.

N-terminal sequencing of the product recovered by this method gave the following correct sequence:
Asp Ser Glu Glu Asp Glu Glu His Thr Ile Ile Thr Asp Thr Glu Leu Pro Pro [SEQ ID NO: 7]
corresponding to authentic mature TFPI at >90% purity.

Figure 1B:
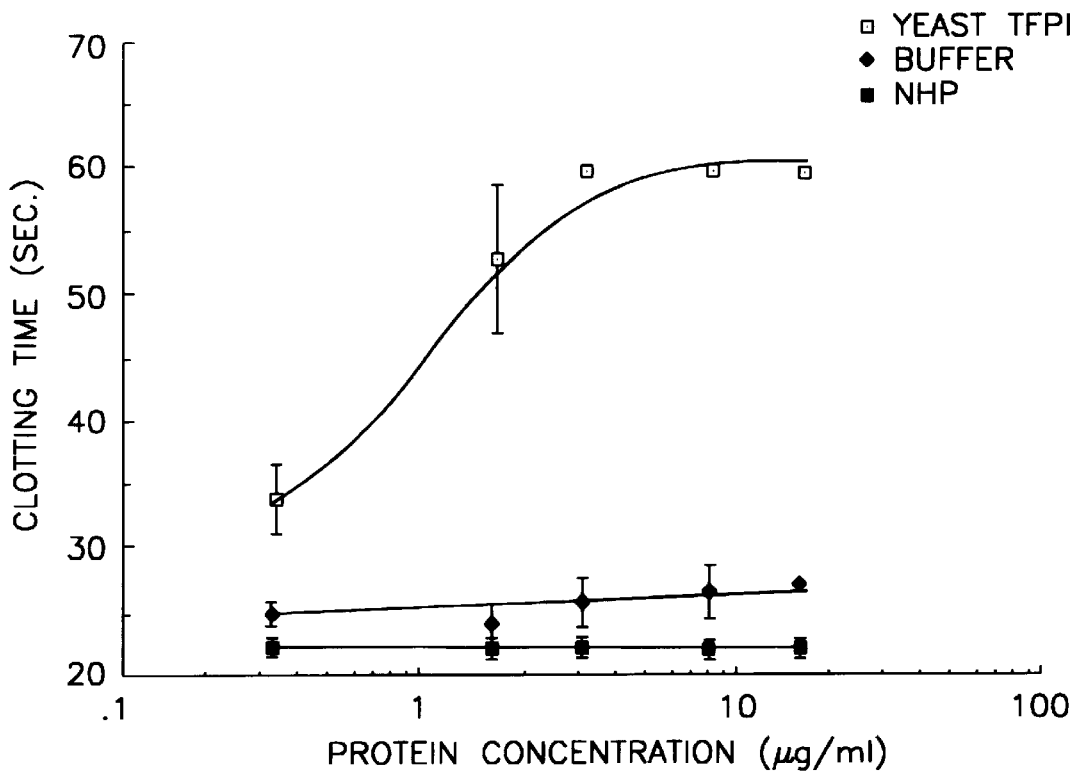
Figure 2:
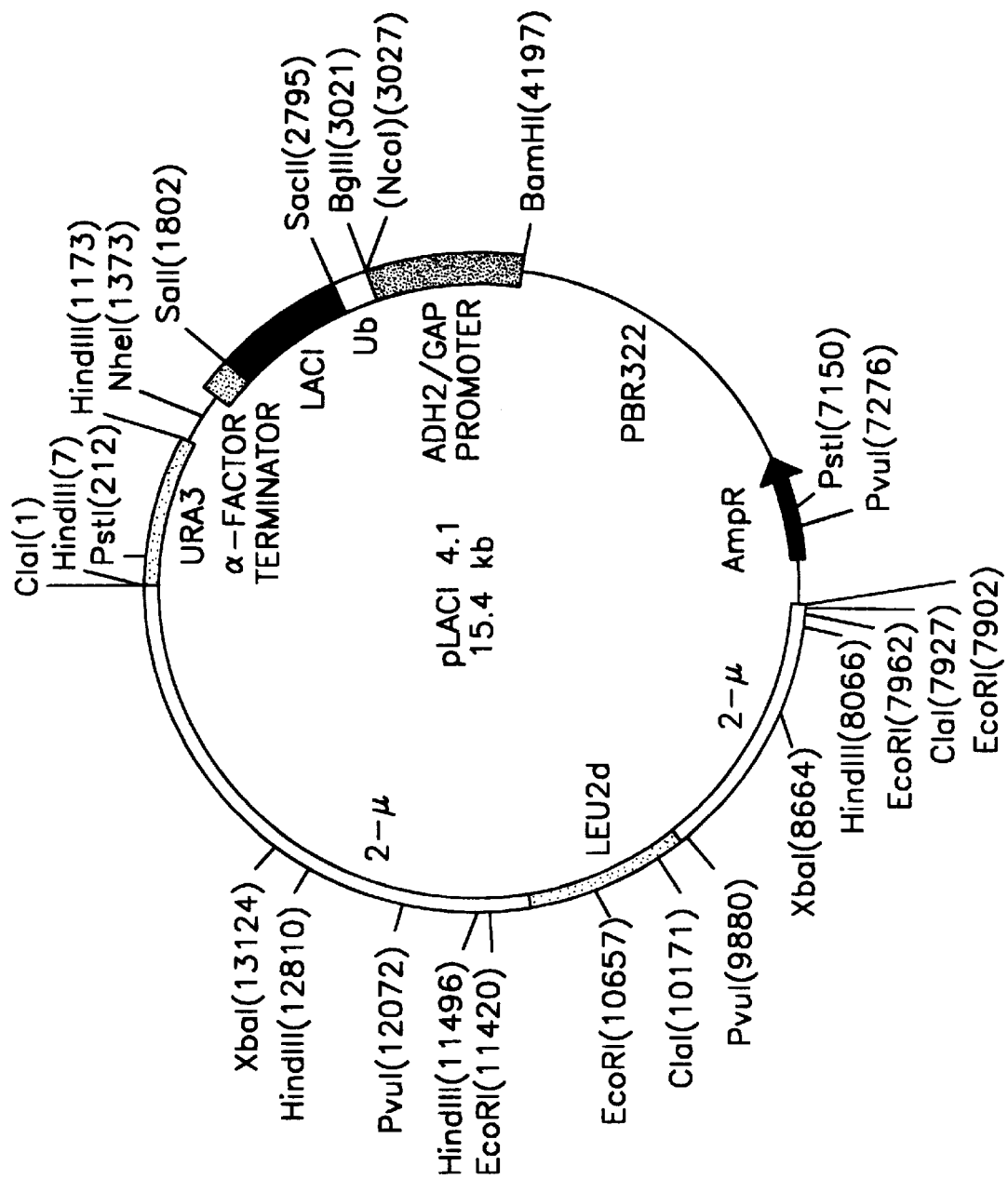
FIG. 2 depicts a schematic of a replicable cloning vehicle (designated pLACI 4.1) including a DNA sequence coding for the TFPI protein.

The recovered product was also tested in the factor Xa amidolytic assay and prothrombin time clotting assays (both described in Wun et al, J. Biol. Chem. 265:16096 (1990)) to assess activity. The data from these assays are displayed in FIGS. 1A and 1B, respectively. PBS buffer was used as a control in the factor Xa Inhibition Assay and PBS buffer as well as normal human serum (NHS) were used as controls in the prothrombin clotting assay. The yeast-produced TFPI inhibited factor Xa activity at a 50% inhibitory concentration of approximately 20 ng/ml and displayed an inhibitory concentration in the prothrombin clotting assay of 1 μg/ml. These results indicate that TFPI produced according to the method of the invention is biologically active.

Example 3

The method of the invention can also be used to produce TFPI in large scale, i.e. 10 liter or greater batches. Yeast strain AB122 was transformed with pLACI 4.1 and grown in selective medium containing Yeast Nitrogen Base without amino acids (Difco), supplemented with 87 mg/L adenine, 43.5 mg/L L-tryptophan, 43.5 mg/L L-histidine, 43.5 mg/L L-arginine, 43.5 mg/L L-methionine, 65.2mg/L L-tyrosine, 109 mg/L L-phenylalanine, 65.2 mg/L-lysine and 8% glucose. Aliquots of the transformed cells were preserved by adding glycerol to 15% and storage at −70° C. S. cerevisiae strain AB122 transformed with pLACI4.1 has was deposited with the ATCC on Jul. 19, 1994 and has been given Accession Number 74291.

Inoculum for the 10 liter fermenter was prepared by addition of 1% v/v frozen, transformed culture into fresh selective media as described in the previous paragraph. The inoculum was then grown in shake flasks for 24–48 hours. Inoculum was then added 0.5% v/v to the contents of a 10 liter fermentation vessel. The media in the vessel contained the following ingredients prior to sterilization:

Tastone 154 Yeast Extract: 10 g/L
Casein Peptone: 20 g/L
Antifoam: 0.3 ml/L
Citric acid: 4 mM
$KH_2POhd 4$: 20 mM
$(NH_4)_2SO_4$: 50 mM
$MnSO_4$: 20 μM
$ZnSO_4$: 20 μM
$H_3BO_3$: 100 μM
$CoCl_2$: 10 μM
$Na_2MoO_4$: 10 μM
$CuSo_4$: 2 μM
Glycerol: 30 g/L.

The contents of the fermentation vessel were then sterilized in situ and the following sterile ingredients added to complete the medium:

$MgSO4$: 20 mM
$FeCl3$: 100 μM
Glucose: 20 g/L
Pyroxidine HCl: 5 mg/L
Thiamine HCl: 10 mg/L
D-Biotin: 0.1 mg/L
Ca Pantothenate: 10 mg/L
Myo-Inositol: 400 mg/L.

During growth of cells in the fermentation vessel, the medium was maintained at a temperature of 30° C. pH 6.0 was maintained by addition of NaOH or phosphoric acid as needed. Agitation was begun at 600 r.p.m. and increased as needed to maintain D.O >30%. Aeration was 1 vvm air. Starting at 15 h after inoculation, a mixture of sterile glucose (25% w/v) and glycerol (6.8% w/v) was added to the fermentor at a rate of 0.1 ml/min/L. At 39 hours, the rate of addition of this mixture was decreased to 0.05 ml/min/L. The culture was terminated at 96 hours. Peak expression of TFPI (1 mg/ml) occurred by 72 h post-inoculation.

The foregoing discussion and examples only illustrate the present invention, persons of ordinary skill in the art will appreciate that the invention can be implemented in other ways, and the invention is defined solely by reference to the claims. Further, all references, patents and patent applications cited in the foregoing specification are incorporated herein by reference.

---

We claim:

1. A method for producing a factor VIIa/TF/Xa binding protein, said method comprising:
    (a) transforming yeast cells with a vehicle, said vehicle comprising a first nucleotide sequence encoding the factor VIIa/TF/Xa binding protein, said factor VIIa/TF/Xa binding protein selected from the group consisting of TFPI and a TFPI mutein, wherein the N-terminal amino acid sequence of the factor VIIa/RF/Xa binding protein is SEQ ID NO: 7, said first nucleotide sequence being immediately preceded in frame by a second nucleotide sequence encoding ubiquitin, the first and second nucleotide sequences together encoding a fusion peptide;
    (b) incubating the transformed yeast cells under conditions favorable for production of the factor VIIa/TF/Xa binding protein, wherein the factor VIIa/TF/Xa binding protein is retained within the yeast cell;
    (c) preparing an insoluble fraction of the transformed yeast cells containing the factor VIIa/TF/Xa binding protein; and
    (d) recovering the factor VIIa/TF/Xa binding protein from the insoluble fraction.

2. The method of claim 1 wherein the factor VIIa/TF/Xa binding protein is expressed in the yeast cell as a fusion protein encoded by SEQ ID 1.

3. The method of claim 1 wherein the yeast cells are of the genus Saccharomyces.

4. The method of claim 3 wherein the yeast cells are of the speices *Saccharomyces cerevisiae* and have a genotype selected from the group consisting of VH6, AB122, and JSC310.

5. The method of claim 1 wherein the factor VIIa/TF/Xa binding protein is TFPI.

6. The method of claim 1 wherein the factor VIIa/TF/Xa binding protein is a mutein of TFPI having arginine in the P1 reactive site of Kunitz-type domain 1.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1065 base pairs
      (B) TYPE: nucleic acid
      (C) STRANDEDNESS: double
      (D) TOPOLOGY: linear (ii) MOLECULE TYPE: other nucleic acid (iii) HYPOTHETICAL: NO (iv) ANTI-SENSE: NO (ix) FEATURE:
      (A) NAME/KEY: CDS
      (B) LOCATION: 1..1056

(xi) SEQUENCE DESCRIPTION: SEQ ID NO:1:

```
ATG CAG ATC TTC GTC AAG ACT TTG ACC GGT AAA ACC ATA ACA TTG GAA        48
Met Gln Ile Phe Val Lys Thr Leu Thr Gly Lys Thr Ile Thr Leu Glu
 1               5                  10                  15

GTT GAA TCT TCC GAT ACC ATC GAC AAC GTT AAG TCG AAA ATT CAA GAC        96
Val Glu Ser Ser Asp Thr Ile Asp Asn Val Lys Ser Lys Ile Gln Asp
                20                  25                  30

AAG GAA GGT ATC CCT CCA GAT CAA CAA AGA TTG ATC TTT GCC GGT AAG       144
Lys Glu Gly Ile Pro Pro Asp Gln Gln Arg Leu Ile Phe Ala Gly Lys
            35                  40                  45

CAG CTA GAA GAC GGT AGA ACG CTG TCT GAT TAC AAC ATT CAG AAG GAG       192
Gln Leu Glu Asp Gly Arg Thr Leu Ser Asp Tyr Asn Ile Gln Lys Glu
        50                  55                  60
```

```
TCC ACC TTA CAT CTT GTG CTA AGG CTC CGC GGT GGT GAT TCT GAG GAA          240
Ser Thr Leu His Leu Val Leu Arg Leu Arg Gly Gly Asp Ser Glu Glu
 65                  70                  75                  80

GAT GAA GAA CAC ACA ATT ATC ACA GAT ACG GAG TTG CCA CCA CTG AAA          288
Asp Glu Glu His Thr Ile Ile Thr Asp Thr Glu Leu Pro Pro Leu Lys
                     85                  90                  95

CTT ATG CAT TCA TTT TGT GCA TTC AAG GCG GAT GAT GGC CCA TGT AAA          336
Leu Met His Ser Phe Cys Ala Phe Lys Ala Asp Asp Gly Pro Cys Lys
                100                 105                 110

GCA ATC ATG AAA AGA TTT TTC TTC AAT ATT TTC ACT CGA CAG TGC GAA          384
Ala Ile Met Lys Arg Phe Phe Phe Asn Ile Phe Thr Arg Gln Cys Glu
            115                 120                 125

GAA TTT ATA TAT GGG GGA TGT GAA GGA AAT CAG AAT CGA TTT GAA AGT          432
Glu Phe Ile Tyr Gly Gly Cys Glu Gly Asn Gln Asn Arg Phe Glu Ser
        130                 135                 140

CTG GAA GAG TGC AAA AAA ATG TGT ACA AGA GAT AAT GCA AAC AGG ATT          480
Leu Glu Glu Cys Lys Lys Met Cys Thr Arg Asp Asn Ala Asn Arg Ile
145                 150                 155                 160

ATA AAG ACA ACA TTG CAA CAA GAA AAG CCA GAT TTC TGC TTT TTG GAA          528
Ile Lys Thr Thr Leu Gln Gln Glu Lys Pro Asp Phe Cys Phe Leu Glu
                165                 170                 175

GAA GAT CCT GGA ATA TGT CGA GGT TAT ATT ACC AGG TAT TTT TAT AAC          576
Glu Asp Pro Gly Ile Cys Arg Gly Tyr Ile Thr Arg Tyr Phe Tyr Asn
            180                 185                 190

AAT CAG ACA AAA CAG TGT GAA CGT TTC AAG TAT GGT GGA TGC CTG GGC          624
Asn Gln Thr Lys Gln Cys Glu Arg Phe Lys Tyr Gly Gly Cys Leu Gly
        195                 200                 205

AAT ATG AAC AAT TTT GAG ACA CTG GAA GAA TGC AAG AAC ATT TGT GAA          672
Asn Met Asn Asn Phe Glu Thr Leu Glu Glu Cys Lys Asn Ile Cys Glu
210                 215                 220

GAT GGT CCG AAT GGT TTC CAG GTG GAT AAT TAT GGA ACC CAG CTC AAT          720
Asp Gly Pro Asn Gly Phe Gln Val Asp Asn Tyr Gly Thr Gln Leu Asn
225                 230                 235                 240

GCT GTG AAT AAC TCC CTG ACT CCG CAA TCA ACC AAG GTT CCC AGC CTT          768
Ala Val Asn Asn Ser Leu Thr Pro Gln Ser Thr Lys Val Pro Ser Leu
                245                 250                 255

TTT GAA TTT CAC GGT CCC TCA TGG TGT CTC ACT CCA GCA GAC AGA GGA          816
Phe Glu Phe His Gly Pro Ser Trp Cys Leu Thr Pro Ala Asp Arg Gly
            260                 265                 270

TTG TGT CGT GCC AAT GAG AAC AGA TTC TAC TAC AAT TCA GTC ATT GGG          864
Leu Cys Arg Ala Asn Glu Asn Arg Phe Tyr Tyr Asn Ser Val Ile Gly
        275                 280                 285

AAA TGC CGC CCA TTT AAG TAC AGT GGA TGT GGG GGA AAT GAA AAC AAT          912
Lys Cys Arg Pro Phe Lys Tyr Ser Gly Cys Gly Gly Asn Glu Asn Asn
290                 295                 300

TTT ACT TCC AAA CAA GAA TGT CTG AGG GCA TGT AAA AAA GGT TTC ATC          960
Phe Thr Ser Lys Gln Glu Cys Leu Arg Ala Cys Lys Lys Gly Phe Ile
305                 310                 315                 320

CAA AGA ATA TCA AAA GGA GGC CTA ATT AAA ACC AAA AGA AAA AGA AAG         1008
Gln Arg Ile Ser Lys Gly Gly Leu Ile Lys Thr Lys Arg Lys Arg Lys
                325                 330                 335

AAG CAG AGA GTG AAA ATA GCA TAT GAA GAA ATT TTT GTT AAA AAT ATG         1056
Lys Gln Arg Val Lys Ile Ala Tyr Glu Glu Ile Phe Val Lys Asn Met
                340                 345                 350

TGAGTCGAC                                                               1065
```

(2) INFORMATION FOR SEQ ID NO:2:

(i) SEQUENCE CHARACTERISTICS:

(A) LENGTH: 352 amino acids
        (B) TYPE: amino acid
        (D) TOPOLOGY: linear (ii) MOLECULE TYPE: protein (xi) SEQUENCE DESCRIPTION: SEQ ID NO:2:

Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ser Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
     50                  55                  60

Ser Thr Leu His Leu Val Leu Arg Leu Arg Gly Gly Asp Ser Glu Glu
 65                  70                  75                  80

Asp Glu Glu His Thr Ile Ile Thr Asp Thr Glu Leu Pro Pro Leu Lys
                 85                  90                  95

Leu Met His Ser Phe Cys Ala Phe Lys Ala Asp Asp Gly Pro Cys Lys
            100                 105                 110

Ala Ile Met Lys Arg Phe Phe Phe Asn Ile Phe Thr Arg Gln Cys Glu
        115                 120                 125

Glu Phe Ile Tyr Gly Gly Cys Glu Gly Asn Gln Asn Arg Phe Glu Ser
    130                 135                 140

Leu Glu Glu Cys Lys Lys Met Cys Thr Arg Asp Asn Ala Asn Arg Ile
145                 150                 155                 160

Ile Lys Thr Thr Leu Gln Gln Glu Lys Pro Asp Phe Cys Phe Leu Glu
                165                 170                 175

Glu Asp Pro Gly Ile Cys Arg Gly Tyr Ile Thr Arg Tyr Phe Tyr Asn
            180                 185                 190

Asn Gln Thr Lys Gln Cys Glu Arg Phe Lys Tyr Gly Gly Cys Leu Gly
        195                 200                 205

Asn Met Asn Asn Phe Glu Thr Leu Glu Glu Cys Lys Asn Ile Cys Glu
    210                 215                 220

Asp Gly Pro Asn Gly Phe Gln Val Asp Asn Tyr Gly Thr Gln Leu Asn
225                 230                 235                 240

Ala Val Asn Asn Ser Leu Thr Pro Gln Ser Thr Lys Val Pro Ser Leu
                245                 250                 255

Phe Glu Phe His Gly Pro Ser Trp Cys Leu Thr Pro Ala Asp Arg Gly
            260                 265                 270

Leu Cys Arg Ala Asn Glu Asn Arg Phe Tyr Tyr Asn Ser Val Ile Gly
        275                 280                 285

Lys Cys Arg Pro Phe Lys Tyr Ser Gly Cys Gly Gly Asn Glu Asn Asn
    290                 295                 300

Phe Thr Ser Lys Gln Glu Cys Leu Arg Ala Cys Lys Lys Gly Phe Ile
305                 310                 315                 320

Gln Arg Ile Ser Lys Gly Gly Leu Ile Lys Thr Lys Arg Lys Arg Lys
                325                 330                 335

Lys Gln Arg Val Lys Ile Ala Tyr Glu Glu Ile Phe Val Lys Asn Met
            340                 345                 350

(2) INFORMATION FOR SEQ ID NO:3:

(i) SEQUENCE CHARACTERISTICS:
        (A) LENGTH: 276 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Arg Ala Ile Met Lys Arg Phe Phe Phe Asn Ile Phe Thr
            35                  40                  45

Arg Gln Cys Glu Glu Phe Ile Tyr Gly Gly Cys Glu Gly Asn Gln Asn
50                      55                  60

Arg Phe Glu Ser Leu Glu Glu Cys Lys Lys Met Cys Thr Arg Asp Asn
65                      70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
            130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
            195                 200                 205

Ser Val Ile Gly Lys Cys Arg Pro Phe Lys Tyr Ser Gly Cys Gly Gly
            210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
            275

(2) INFORMATION FOR SEQ ID NO:4:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

CCGCGGGGC                                                              9

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

GCTCCGCGGT GGCGATTCTG AGG        23

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

TCTGTCGACT CACATATTTT TAAC        24

(2) INFORMATION FOR SEQ ID NO:7:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Asp Ser Glu Glu Asp Glu Glu His Thr Ile Ile Thr Asp Thr Glu Leu
1             5                   10               15

Pro Pro